(12) United States Patent
Meyer et al.

(10) Patent No.: US 8,417,374 B2
(45) Date of Patent: Apr. 9, 2013

(54) METHOD AND APPARATUS FOR CHANGING SPEED OR DIRECTION OF AN ARTICLE

(75) Inventors: Thomas C. Meyer, Elkhart Lake, WI (US); Peter J. Jenquin, Plymouth, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 308 days.

(21) Appl. No.: 12/799,479

(22) Filed: Apr. 26, 2010

(65) Prior Publication Data
US 2010/0263987 A1  Oct. 21, 2010

Related U.S. Application Data

(63) Continuation-in-part of application No. 11/104,316, filed on Apr. 12, 2005, now Pat. No. 7,703,599.

(60) Provisional application No. 60/563,511, filed on Apr. 19, 2004.

(51) Int. Cl.
*G06F 7/00* (2006.01)

(52) U.S. Cl. .................................. 700/230; 198/457.03

(58) Field of Classification Search .................. 700/230; 198/369.7, 369.1, 457.06, 600, 408, 409, 198/412
See application file for complete search history.

(56) References Cited

U.S. PATENT DOCUMENTS

| | | | |
|---|---|---|---|
| 135,145 A | 1/1873 | Murphy | |
| 293,353 A | 2/1884 | Purvis | |
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,431,315 A | 10/1922 | Le Moine | |

(Continued)

FOREIGN PATENT DOCUMENTS

| | | |
|---|---|---|
| BE | 1007854 | 11/1995 |
| CA | 1146129 | 5/1983 |

(Continued)

OTHER PUBLICATIONS

USPTO Office Action dated May 4, 2007 regarding U.S. Appl. No. 11/104,316, 8 pages.

(Continued)

*Primary Examiner* — Ramya Burgess
(74) *Attorney, Agent, or Firm* — Ryan Kromholz & Manion, S.C.

(57) ABSTRACT

A method of reversing direction of an article, or of speeding up or slowing down an article is disclosed by engaging an article with a first belt to move the article in a first direction; disengaging the article from the first belt; and then engaging the article with a second belt to move the article at a different speed. An apparatus to change speed of an article is also disclosed by a first belt rotating in a first direction; a second belt rotating in the direction at a second speed; the first belt engaging an article at a first time while the second belt is disengaged with the article, the first belt disengaging the article at a second time, and the second belt engaging the article at a third time while the first belt is disengaged with the article.

3 Claims, 12 Drawing Sheets

U.S. PATENT DOCUMENTS

| | | |
|---|---|---|
| 1,605,842 A | 11/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 9/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,089,494 A | 5/1963 | Schwartz |
| 3,091,408 A | 5/1963 | Schorneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerie |
| 3,758,102 A | 9/1973 | Munn et al. |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Geller et al. |
| 3,903,768 A | 9/1975 | Amberg et al. |
| 3,904,147 A | 9/1975 | Tartel et al. |
| 3,918,698 A | 11/1975 | Coast |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |

| | | | | | |
|---|---|---|---|---|---|
| 4,522,853 A | 6/1985 | Szonn et al. | 5,147,487 A | 9/1992 | Nomura et al. |
| 4,543,152 A | 9/1985 | Nozaka | 5,163,594 A | 11/1992 | Meyer |
| 4,551,191 A | 11/1985 | Kock et al. | 5,171,239 A | 12/1992 | Igaue et al. |
| 4,586,199 A | 5/1986 | Birring | 5,176,244 A | 1/1993 | Radzins et al. |
| 4,589,945 A | 5/1986 | Polit | 5,183,252 A | 2/1993 | Wolber et al. |
| 4,603,800 A | 8/1986 | Focke et al. | 5,188,627 A | 2/1993 | Igaue et al. |
| 4,608,115 A | 8/1986 | Schroth et al. | 5,190,234 A | 3/1993 | Ezekiel |
| 4,610,681 A | 9/1986 | Strohbeen et al. | 5,195,684 A | 3/1993 | Radzins |
| 4,610,682 A | 9/1986 | Kopp | 5,203,043 A | 4/1993 | Riedel |
| 4,614,076 A | 9/1986 | Rathemacher | 5,213,645 A | 5/1993 | Nomura et al. |
| 4,619,357 A | 10/1986 | Radzins et al. | 5,222,422 A | 6/1993 | Benner, Jr. et al. |
| 4,634,482 A | 1/1987 | Lammers | 5,223,069 A | 6/1993 | Tokuno et al. |
| 4,641,381 A | 2/1987 | Heran et al. | 5,226,992 A | 7/1993 | Morman |
| 4,642,150 A | 2/1987 | Stemmler | 5,246,433 A | 9/1993 | Hasse et al. |
| 4,642,839 A | 2/1987 | Urban | 5,252,228 A | 10/1993 | Stokes |
| 4,650,530 A | 3/1987 | Mahoney et al. | 5,267,933 A | 12/1993 | Precoma |
| 4,663,220 A | 5/1987 | Wisneski et al. | 5,273,228 A | 12/1993 | Yoshida |
| 4,672,705 A | 6/1987 | Bors et al. | 5,275,676 A | 1/1994 | Rooyakkers et al. |
| 4,675,016 A | 6/1987 | Meuli et al. | 5,308,345 A | 5/1994 | Herrin |
| 4,675,062 A | 6/1987 | Instance | 5,328,438 A | 7/1994 | Crowley |
| 4,675,068 A | 6/1987 | Lundmark | 5,340,424 A | 8/1994 | Matsushita |
| 4,686,136 A | 8/1987 | Homonoff et al. | 5,368,893 A | 11/1994 | Sommer et al. |
| 4,693,056 A | 9/1987 | Raszewski | 5,389,173 A | 2/1995 | Merkotoris et al. |
| 4,701,239 A | 10/1987 | Craig | 5,393,360 A | 2/1995 | Bridges et al. |
| 4,720,415 A | 1/1988 | Vander Wielen et al. | 5,407,507 A | 4/1995 | Ball |
| 4,723,698 A | 2/1988 | Schoonderbeek | 5,407,513 A | 4/1995 | Hayden et al. |
| 4,726,874 A | 2/1988 | Van Vliet | 5,415,649 A | 5/1995 | Watanabe et al. |
| 4,726,876 A | 2/1988 | Tomsovic et al. | 5,421,924 A | 6/1995 | Ziegelhoffer et al. |
| 4,743,241 A | 5/1988 | Igaue et al. | 5,424,025 A | 6/1995 | Hanschen et al. |
| 4,751,997 A | 6/1988 | Hirsch | 5,429,576 A | 7/1995 | Doderer-Winkler |
| 4,753,429 A | 6/1988 | Irvine et al. | 5,435,802 A | 7/1995 | Kober |
| 4,756,141 A | 7/1988 | Hirsch et al. | 5,449,353 A | 9/1995 | Watanabe et al. |
| 4,764,325 A | 8/1988 | Angstadt | 5,464,401 A | 11/1995 | Hasse et al. |
| 4,765,780 A | 8/1988 | Angstadt | 5,486,253 A | 1/1996 | Otruba |
| 4,776,920 A | 10/1988 | Ryan | 5,494,622 A | 2/1996 | Heath et al. |
| 4,777,513 A | 10/1988 | Nelson | 5,500,075 A | 3/1996 | Herrmann |
| 4,782,647 A | 11/1988 | Williams et al. | 5,516,392 A | 5/1996 | Bridges et al. |
| 4,785,986 A | 11/1988 | Daane et al. | 5,518,566 A | 5/1996 | Bridges et al. |
| 4,795,451 A | 1/1989 | Buckley | 5,525,175 A | 6/1996 | Blenke et al. |
| 4,795,510 A | 1/1989 | Wittrock et al. | 5,531,850 A | 7/1996 | Herrmann |
| 4,798,353 A | 1/1989 | Peugh | 5,540,647 A | 7/1996 | Weiermann et al. |
| 4,801,345 A | 1/1989 | Dussaud et al. | 5,545,275 A | 8/1996 | Herrin et al. |
| 4,802,570 A | 2/1989 | Hirsch et al. | 5,545,285 A | 8/1996 | Johnson |
| 4,840,609 A | 6/1989 | Jones et al. | 5,552,013 A | 9/1996 | Ehlert et al. |
| 4,845,964 A | 7/1989 | Bors et al. | 5,556,360 A | 9/1996 | Kober et al. |
| 4,864,802 A | 9/1989 | D'Angelo | 5,556,504 A | 9/1996 | Rajala et al. |
| 4,880,102 A | 11/1989 | Indrebo | 5,560,793 A | 10/1996 | Ruscher et al. |
| 4,888,231 A | 12/1989 | Angstadt | 5,575,187 A | 11/1996 | Dieterlen |
| 4,892,536 A | 1/1990 | DesMarais et al. | 5,586,964 A | 12/1996 | Chase |
| 4,904,440 A | 2/1990 | Angstadt | 5,602,747 A | 2/1997 | Rajala |
| 4,908,175 A | 3/1990 | Angstadt | 5,603,794 A | 2/1997 | Thomas |
| 4,909,019 A | 3/1990 | Delacretaz et al. | 5,624,420 A | 4/1997 | Bridges et al. |
| 4,915,767 A | 4/1990 | Rajala et al. | 5,624,428 A | 4/1997 | Sauer |
| 4,917,746 A | 4/1990 | Kons | 5,628,738 A | 5/1997 | Suekane |
| 4,925,520 A | 5/1990 | Beaudoin et al. | 5,634,917 A | 6/1997 | Fujioka et al. |
| 4,927,322 A | 5/1990 | Schweizer et al. | 5,643,165 A | 7/1997 | Klekamp |
| 4,927,486 A | 5/1990 | Fattal et al. | 5,643,396 A | 7/1997 | Rajala et al. |
| 4,927,582 A | 5/1990 | Bryson | 5,645,543 A | 7/1997 | Nomura et al. |
| 4,937,887 A | 7/1990 | Schreiner | 5,659,229 A | 8/1997 | Rajala |
| 4,963,072 A | 10/1990 | Miley et al. | 5,660,657 A | 8/1997 | Rajala et al. |
| 4,987,940 A | 1/1991 | Straub et al. | 5,660,665 A | 8/1997 | Jalonen |
| 4,994,010 A | 2/1991 | Doderer-Winkler | 5,683,376 A | 11/1997 | Kato et al. |
| 5,000,806 A | 3/1991 | Merkatoris et al. | 5,683,531 A | 11/1997 | Roessler et al. |
| 5,021,111 A | 6/1991 | Swenson | RE35,687 E | 12/1997 | Igaue et al. |
| 5,025,910 A | 6/1991 | Lasure et al. | 5,693,165 A | 12/1997 | Schmitz |
| 5,045,039 A | 9/1991 | Bay | 5,699,653 A | 12/1997 | Hartman et al. |
| 5,062,597 A | 11/1991 | Martin et al. | 5,705,013 A | 1/1998 | Nease |
| 5,064,179 A | 11/1991 | Martin | 5,707,470 A | 1/1998 | Rajala et al. |
| 5,064,492 A | 11/1991 | Friesch | 5,711,832 A | 1/1998 | Glaug et al. |
| 5,080,741 A | 1/1992 | Nomura et al. | 5,725,518 A | 3/1998 | Coates |
| 5,094,658 A | 3/1992 | Smithe et al. | 5,725,714 A | 3/1998 | Fujioka |
| 5,096,532 A | 3/1992 | Neuwirth et al. | 5,743,994 A | 4/1998 | Roessler et al. |
| 5,108,017 A | 4/1992 | Adamski et al. | 5,745,922 A | 5/1998 | Rajala et al. |
| 5,109,767 A | 5/1992 | Nyfeler et al. | 5,746,869 A | 5/1998 | Hayden et al. |
| 5,110,403 A | 5/1992 | Ehlert | 5,749,989 A | 5/1998 | Linman et al. |
| 5,127,981 A | 7/1992 | Straub et al. | 5,766,389 A | 6/1998 | Brandon et al. |
| 5,131,525 A | 7/1992 | Musschoot | 5,788,797 A | 8/1998 | Herrin et al. |
| 5,131,901 A | 7/1992 | Moll | 5,817,199 A | 10/1998 | Brennecke et al. |
| 5,133,511 A | 7/1992 | Mack | 5,829,164 A | 11/1998 | Kotischke |

| | | | | | | |
|---|---|---|---|---|---|---|
| 5,836,931 A | 11/1998 | Toyoda et al. | | 6,659,991 B2 | 12/2003 | Suekane |
| 5,858,012 A | 1/1999 | Yamaki et al. | | 6,675,552 B2 | 1/2004 | Kunz et al. |
| 5,865,393 A | 2/1999 | Kreft et al. | | 6,684,925 B2 | 2/2004 | Nagate et al. |
| 5,868,727 A | 2/1999 | Barr et al. | | 6,722,494 B2 | 4/2004 | Nakakado |
| 5,876,027 A | 3/1999 | Fukui et al. | | 6,730,189 B1 | 5/2004 | Franzmann |
| 5,876,792 A | 3/1999 | Caldwell | | 6,743,324 B2 | 6/2004 | Hargett et al. |
| 5,879,500 A | 3/1999 | Herrin et al. | | 6,750,466 B2 | 6/2004 | Guha et al. |
| 5,902,431 A | 5/1999 | Wilkinson et al. | | 6,758,109 B2 | 7/2004 | Nakakado |
| 5,932,039 A | 8/1999 | Popp et al. | | 6,766,817 B2 | 7/2004 | da Silva |
| 5,938,193 A | 8/1999 | Bluemle et al. | | 6,808,582 B2 | 10/2004 | Popp et al. |
| 5,964,390 A | 10/1999 | Boerresen et al. | | D497,991 S | 11/2004 | Otsubo et al. |
| 5,964,970 A | 10/1999 | Woolwine et al. | | 6,814,217 B2 | 11/2004 | Blumenthal et al. |
| 5,971,134 A * | 10/1999 | Trefz et al. ............... 198/460.1 | | 6,820,671 B2 | 11/2004 | Calvert |
| 6,022,443 A | 2/2000 | Rajala et al. | | 6,837,840 B2 | 1/2005 | Yonekawa et al. |
| 6,036,805 A | 3/2000 | McNichols | | 6,840,616 B2 | 1/2005 | Summers |
| 6,043,836 A | 3/2000 | Kerr et al. | | 6,852,186 B1 | 2/2005 | Matsuda et al. |
| 6,050,517 A | 4/2000 | Dobrescu et al. | | 6,875,202 B2 | 4/2005 | Kumasaka et al. |
| 6,074,110 A | 6/2000 | Verlinden et al. | | 6,893,528 B2 | 5/2005 | Middelstadt et al. |
| 6,076,442 A | 6/2000 | Arterburn et al. | | 6,913,718 B2 | 7/2005 | Ducker |
| 6,098,249 A | 8/2000 | Toney et al. | | 6,918,404 B2 | 7/2005 | Dias da Silva |
| 6,123,792 A | 9/2000 | Samida et al. | | 6,976,521 B2 | 12/2005 | Mlinar |
| 6,171,432 B1 | 1/2001 | Brisebois | | 6,978,486 B2 | 12/2005 | Zhou et al. |
| 6,183,576 B1 | 2/2001 | Couillard et al. | | 7,017,321 B2 * | 3/2006 | Salvoni ............... 53/76 |
| 6,193,054 B1 * | 2/2001 | Henson et al. ............... 198/783 | | 7,017,820 B1 | 3/2006 | Brunner |
| 6,195,850 B1 | 3/2001 | Melbye | | 7,045,031 B2 | 5/2006 | Popp et al. |
| 6,210,386 B1 | 4/2001 | Inoue | | 7,066,586 B2 | 6/2006 | da Silva |
| 6,212,859 B1 | 4/2001 | Bielik, Jr. et al. | | 7,077,393 B2 | 7/2006 | Ishida |
| 6,214,147 B1 | 4/2001 | Mortellite et al. | | 7,130,710 B2 | 10/2006 | Popp et al. |
| 6,250,048 B1 | 6/2001 | Linkiewicz | | 7,172,666 B2 | 2/2007 | Groves et al. |
| 6,264,784 B1 | 7/2001 | Menard et al. | | 7,195,684 B2 | 3/2007 | Satoh |
| 6,276,421 B1 | 8/2001 | Valenti et al. | | 7,201,345 B2 | 4/2007 | Werner |
| 6,276,587 B1 | 8/2001 | Boerresen | | 7,214,174 B2 | 5/2007 | Allen et al. |
| 6,284,081 B1 | 9/2001 | Vogt et al. | | 7,214,287 B2 | 5/2007 | Shiomi |
| 6,287,409 B1 | 9/2001 | Stephany | | 7,247,219 B2 | 7/2007 | O'Dowd |
| 6,306,122 B1 | 10/2001 | Narawa et al. | | 7,303,708 B2 | 12/2007 | Andrews et al. |
| 6,309,336 B1 | 10/2001 | Muessig et al. | | 7,332,459 B2 * | 2/2008 | Collins et al. ............... 507/224 |
| 6,312,420 B1 | 11/2001 | Sasaki et al. | | 7,380,213 B2 | 5/2008 | Pokorny et al. |
| 6,314,333 B1 | 11/2001 | Rajala et al. | | 7,398,870 B2 | 7/2008 | McCabe |
| 6,315,022 B1 | 11/2001 | Herrin et al. | | 7,449,084 B2 | 11/2008 | Nakakado |
| 6,319,347 B1 | 11/2001 | Rajala | | 7,452,436 B2 | 11/2008 | Andrews |
| 6,336,921 B1 | 1/2002 | Kato et al. | | 7,533,709 B2 | 5/2009 | Meyer |
| 6,358,350 B1 | 3/2002 | Glaug et al. | | 7,537,215 B2 | 5/2009 | Beaudoin et al. |
| 6,369,291 B1 | 4/2002 | Uchimoto et al. | | 7,587,966 B2 | 9/2009 | Nakakado et al. |
| 6,375,769 B1 | 4/2002 | Quereshi et al. | | 7,618,513 B2 | 11/2009 | Meyer |
| 6,391,013 B1 | 5/2002 | Suzuki et al. | | 7,638,014 B2 | 12/2009 | Coose et al. |
| 6,416,697 B1 | 7/2002 | Venturino et al. | | 7,640,962 B2 | 1/2010 | Meyer et al. |
| 6,431,038 B2 | 8/2002 | Couturier | | 7,703,599 B2 | 4/2010 | Meyer |
| 6,440,246 B1 | 8/2002 | Vogt et al. | | 7,708,849 B2 | 5/2010 | McCabe |
| 6,443,389 B1 | 9/2002 | Palone | | 7,770,712 B2 | 8/2010 | McCabe |
| 6,446,795 B1 | 9/2002 | Allen et al. | | 7,771,407 B2 | 8/2010 | Umebayashi |
| 6,473,669 B2 | 10/2002 | Rajala et al. | | 7,780,052 B2 | 8/2010 | McCabe |
| 6,475,325 B1 | 11/2002 | Parrish et al. | | 7,793,772 B2 * | 9/2010 | Schafer ............... 198/460.1 |
| 6,478,786 B1 | 11/2002 | Gluag et al. | | 7,811,403 B2 | 10/2010 | Andrews |
| 6,482,278 B1 | 11/2002 | McCabe et al. | | 7,861,756 B2 | 1/2011 | Jenquin et al. |
| 6,494,244 B2 | 12/2002 | Parrish et al. | | 7,871,400 B2 | 1/2011 | Sablone et al. |
| 6,514,233 B1 | 2/2003 | Glaug | | 7,909,956 B2 | 3/2011 | Coose et al. |
| 6,521,320 B2 | 2/2003 | McCabe et al. | | 7,975,584 B2 | 7/2011 | McCabe |
| 6,523,595 B1 | 2/2003 | Milner et al. | | 7,987,964 B2 | 8/2011 | McCabe |
| 6,524,423 B1 | 2/2003 | Hilt et al. | | 8,007,484 B2 | 8/2011 | McCabe et al. |
| 6,533,879 B2 | 3/2003 | Quereshi et al. | | 8,007,623 B2 | 8/2011 | Andrews |
| 6,540,857 B1 | 4/2003 | Coenen et al. | | 8,011,493 B2 | 9/2011 | Giuliani et al. |
| 6,547,909 B1 | 4/2003 | Butterworth | | 8,016,972 B2 | 9/2011 | Andrews et al. |
| 6,551,228 B1 | 4/2003 | Richards | | 2001/0012813 A1 | 8/2001 | Bluemle |
| 6,551,430 B1 | 4/2003 | Glaug et al. | | 2001/0017181 A1 | 8/2001 | Otruba et al. |
| 6,554,815 B1 | 4/2003 | Umebayashi | | 2001/0035332 A1 * | 11/2001 | Zeitler ............... 198/464.3 |
| 6,569,275 B1 | 5/2003 | Popp et al. | | 2002/0046802 A1 | 4/2002 | Tachibana et al. |
| 6,572,520 B2 | 6/2003 | Blumle | | 2002/0059013 A1 | 5/2002 | Rajala et al. |
| 6,581,517 B1 | 6/2003 | Becker et al. | | 2002/0096241 A1 | 7/2002 | Instance |
| 6,585,841 B1 | 7/2003 | Popp et al. | | 2002/0125105 A1 | 9/2002 | Nakakado |
| 6,589,149 B1 | 7/2003 | VanEperen et al. | | 2002/0162776 A1 | 11/2002 | Hergeth |
| 6,596,107 B2 | 7/2003 | Stopher | | 2003/0000620 A1 | 1/2003 | Herrin et al. |
| 6,596,108 B2 | 7/2003 | McCabe | | 2003/0015209 A1 | 1/2003 | Gingras et al. |
| 6,605,172 B1 | 8/2003 | Anderson et al. | | 2003/0051802 A1 | 3/2003 | Hargett et al. |
| 6,605,173 B2 | 8/2003 | Glaug et al. | | 2003/0052148 A1 | 3/2003 | Rajala et al. |
| 6,637,583 B1 | 10/2003 | Anderson | | 2003/0066585 A1 | 4/2003 | McCabe |
| 6,648,122 B1 | 11/2003 | Hirsch et al. | | 2003/0083638 A1 | 5/2003 | Molee |
| 6,649,010 B2 | 11/2003 | Parrish et al. | | 2003/0084984 A1 | 5/2003 | Glaug et al. |
| 6,656,309 B1 | 12/2003 | Parker et al. | | 2003/0089447 A1 | 5/2003 | Molee et al. |
| 6,659,150 B1 | 12/2003 | Perkins et al. | | 2003/0121614 A1 | 7/2003 | Tabor et al. |

| | | | |
|---|---|---|---|
| 2003/0135189 A1 | 7/2003 | Umebayashi | |
| 2004/0007328 A1 | 1/2004 | Popp et al. | |
| 2004/0016500 A1 | 1/2004 | Tachibana et al. | |
| 2004/0044325 A1 | 3/2004 | Corneliusson | |
| 2004/0087425 A1 | 5/2004 | Ng et al. | |
| 2004/0112517 A1 | 6/2004 | Groves et al. | |
| 2004/0164482 A1 | 8/2004 | Edinger | |
| 2004/0182497 A1 | 9/2004 | Lowrey | |
| 2005/0000628 A1 | 1/2005 | Norrley | |
| 2005/0022476 A1 | 2/2005 | Hamer | |
| 2005/0077418 A1 | 4/2005 | Werner et al. | |
| 2005/0196538 A1 | 9/2005 | Sommer et al. | |
| 2005/0230056 A1 | 10/2005 | Meyer et al. | |
| 2005/0230449 A1 | 10/2005 | Meyer et al. | |
| 2005/0233881 A1 | 10/2005 | Meyer | |
| 2005/0234412 A1 | 10/2005 | Andrews et al. | |
| 2005/0257881 A1 | 11/2005 | Coose et al. | |
| 2005/0275148 A1 | 12/2005 | Beaudoin et al. | |
| 2006/0021300 A1 | 2/2006 | Tada et al. | |
| 2006/0137298 A1 | 6/2006 | Oshita et al. | |
| 2006/0224137 A1 | 10/2006 | McCabe et al. | |
| 2006/0265867 A1 | 11/2006 | Schaap | |
| 2007/0074953 A1 | 4/2007 | McCabe | |
| 2008/0223537 A1 | 9/2008 | Wiedmann | |
| 2009/0020211 A1 | 1/2009 | Andrews et al. | |
| 2010/0078119 A1 | 4/2010 | Yamamoto | |
| 2010/0078120 A1 | 4/2010 | Otsubo | |
| 2010/0078127 A1 | 4/2010 | Yamamoto | |
| 2010/0193138 A1 | 8/2010 | Eckstein | |
| 2010/0193155 A1 | 8/2010 | Nakatani | |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 4/2006 |
| CA | 2559517 | 5/2007 |
| CA | 2337700 | 8/2008 |
| CA | 2407867 | 6/2010 |
| DE | 60123502 | 10/2006 |
| DE | 60216550 | 12/2006 |
| DE | 102005048868 | 4/2007 |
| DE | 102006047280 | 4/2007 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 8/1987 |
| EP | 439897 | 2/1990 |
| EP | 455231 | 11/1991 |
| EP | 510251 | 10/1992 |
| EP | 0652175 | 5/1995 |
| EP | 0811473 | 12/1997 |
| EP | 0901780 | 3/1999 |
| EP | 0439897 | 8/1999 |
| EP | 990588 | 4/2000 |
| EP | 1132325 | 9/2001 |
| EP | 1199057 | 4/2002 |
| EP | 1272347 | 1/2003 |
| EP | 1366734 | 12/2003 |
| EP | 1571249 | 9/2005 |
| EP | 1619008 | 1/2006 |
| EP | 1707168 | 4/2006 |
| EP | 1726414 | 11/2006 |
| EP | 1302424 | 12/2006 |
| EP | 1801045 | 6/2007 |
| EP | 1941853 | 7/2008 |
| EP | 2233116 | 9/2010 |
| EP | 2238955 | 10/2010 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |
| FR | 2255961 | 7/1975 |
| FR | 1132325 | 10/2006 |
| FR | 2891811 | 4/2007 |
| GB | 191101501 | 1/1912 |
| GB | 439897 | 12/1935 |
| GB | 856389 | 12/1960 |
| GB | 941073 | 11/1963 |
| GB | 1096573 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 9299398 | 11/1997 |
| JP | 10035621 | 2/1998 |
| JP | 10-277091 | 10/1998 |
| SE | 0602047 | 5/2007 |
| SE | 0601003-7 | 6/2007 |
| SE | 0601145-6 | 10/2009 |
| WO | WO2008155618 | 12/1988 |
| WO | WO9403301 | 2/1994 |
| WO | WO9732552 | 9/1997 |
| WO | WO 9747810 | 12/1997 |
| WO | WO9821134 | 5/1998 |
| WO | WO 9907319 | 2/1999 |
| WO | WO 9913813 | 3/1999 |
| WO | WO9932385 | 7/1999 |
| WO | WO 9965437 | 12/1999 |
| WO | WO 0143682 | 6/2001 |
| WO | WO 0172237 | 10/2001 |
| WO | WO2004007329 | 1/2004 |
| WO | WO 2005075163 | 1/2005 |
| WO | WO2007029115 | 3/2007 |
| WO | WO2007039800 | 4/2007 |
| WO | WO2007126347 | 11/2007 |
| WO | WO2008001209 | 1/2008 |

OTHER PUBLICATIONS

USPTO Office Action dated Apr. 2, 2008 regarding U.S. Appl. No. 11/104,316, 5 pages.

USPTO Office Action dated Nov. 26, 2008 regarding U.S. Appl. No. 11/104,316, 6 pages.

USPTO Office Action dated Jun. 24, 2009 regarding U.S. Appl. No. 11/104,316, 6 pages.

USPTO Office Action dated Dec. 8, 2009 regarding U.S. Appl. No. 11/104,316, 5 pages.

USPTO Notice of Allowance, with Examiner's Amendment, dated Jan. 26, 2010 regarding U.S. Appl. No. 11/104,316, 6 pages.

* cited by examiner

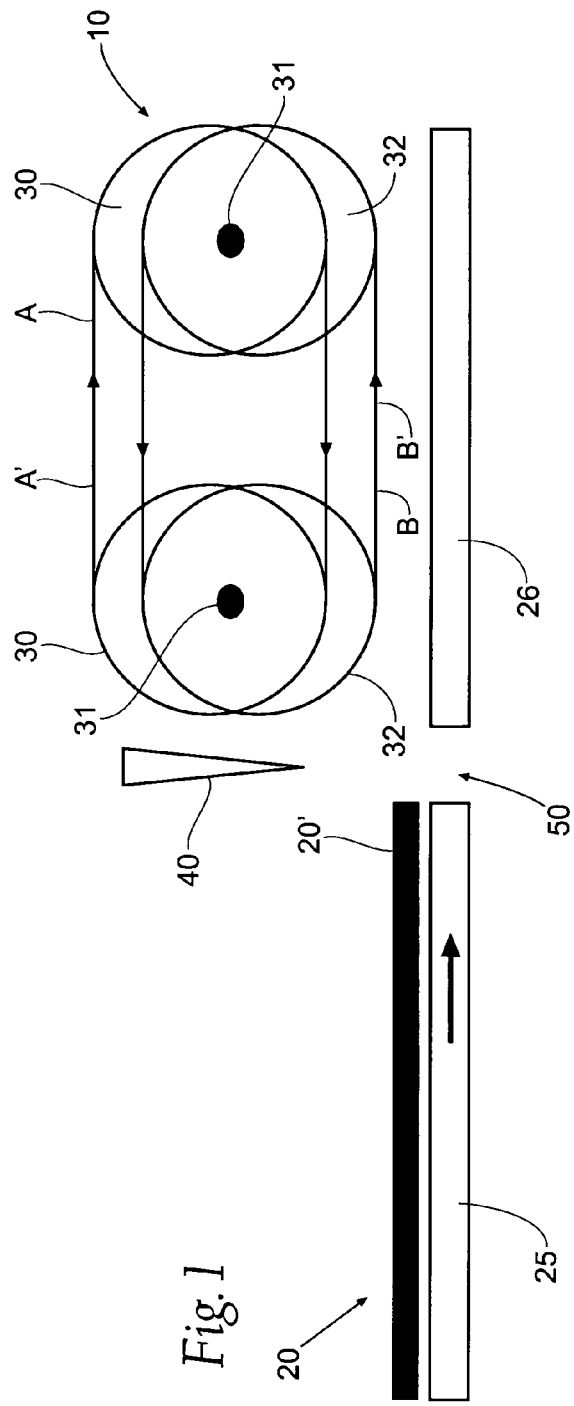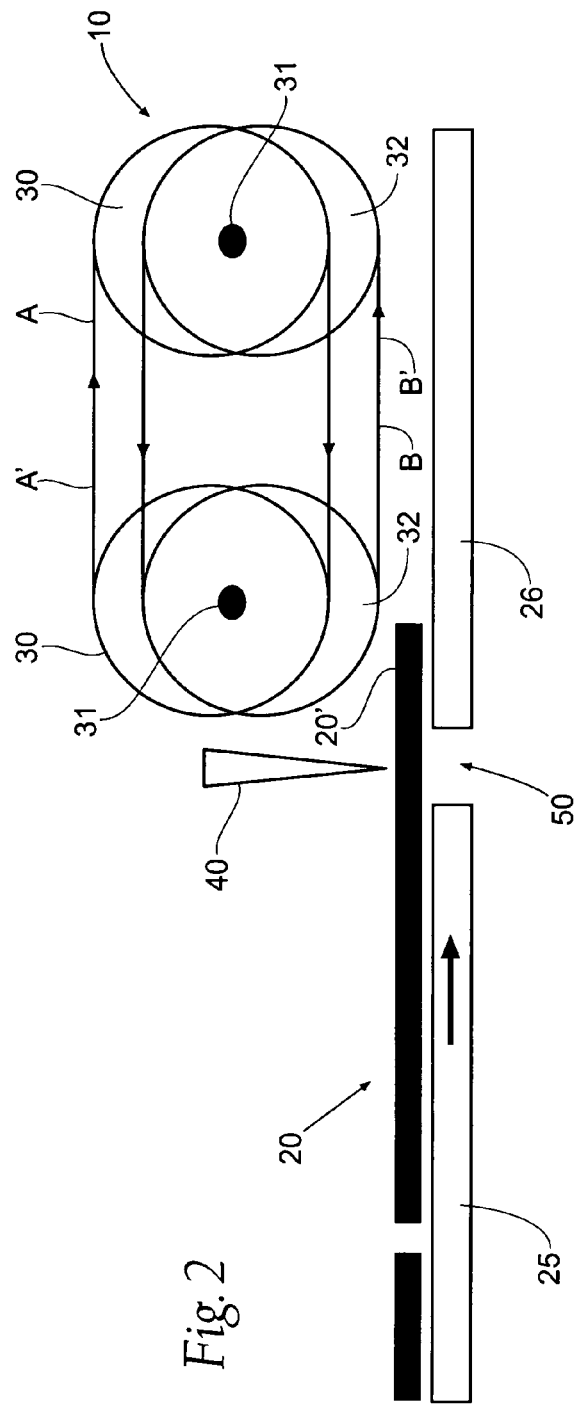
Fig.1
Fig.2

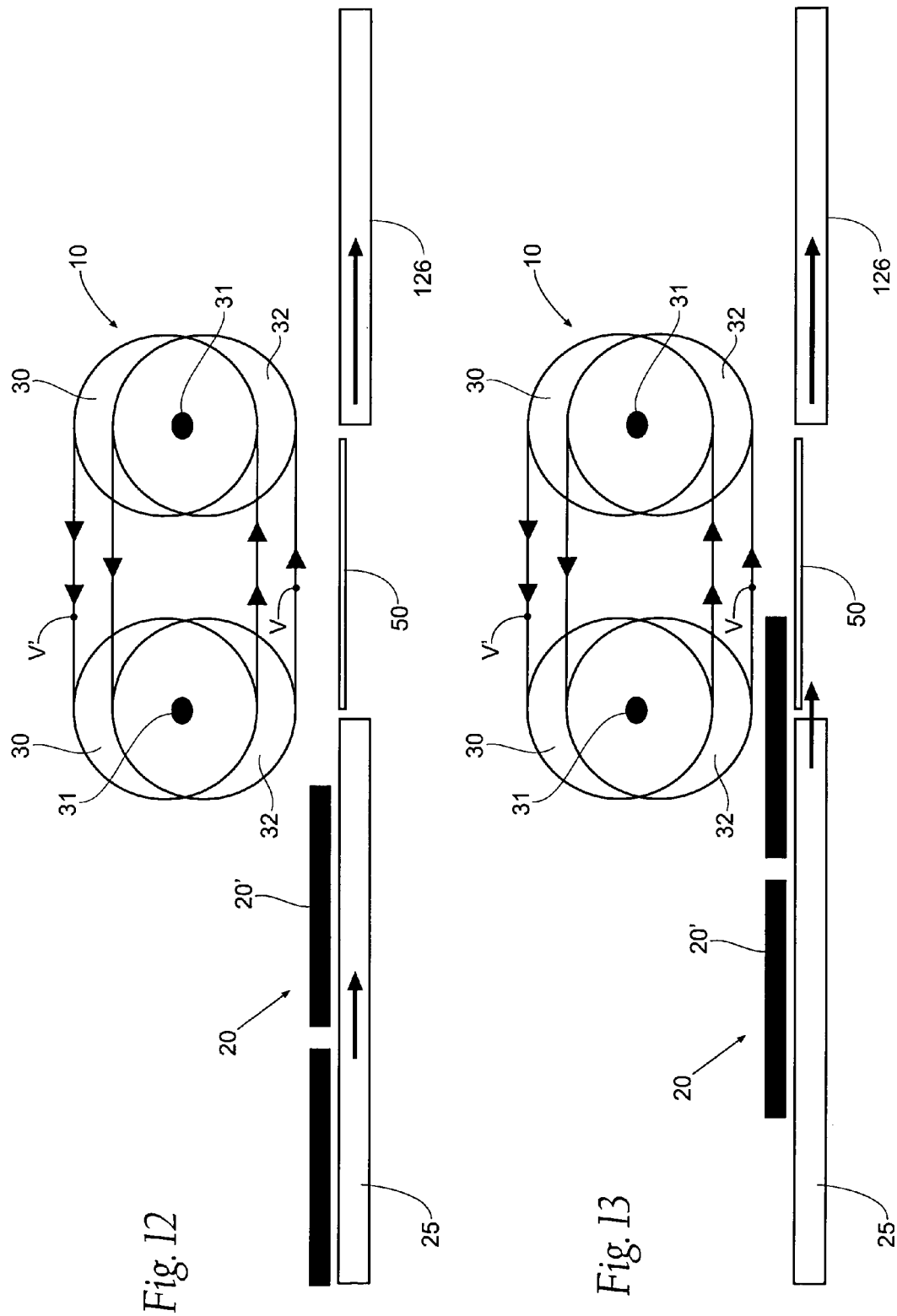

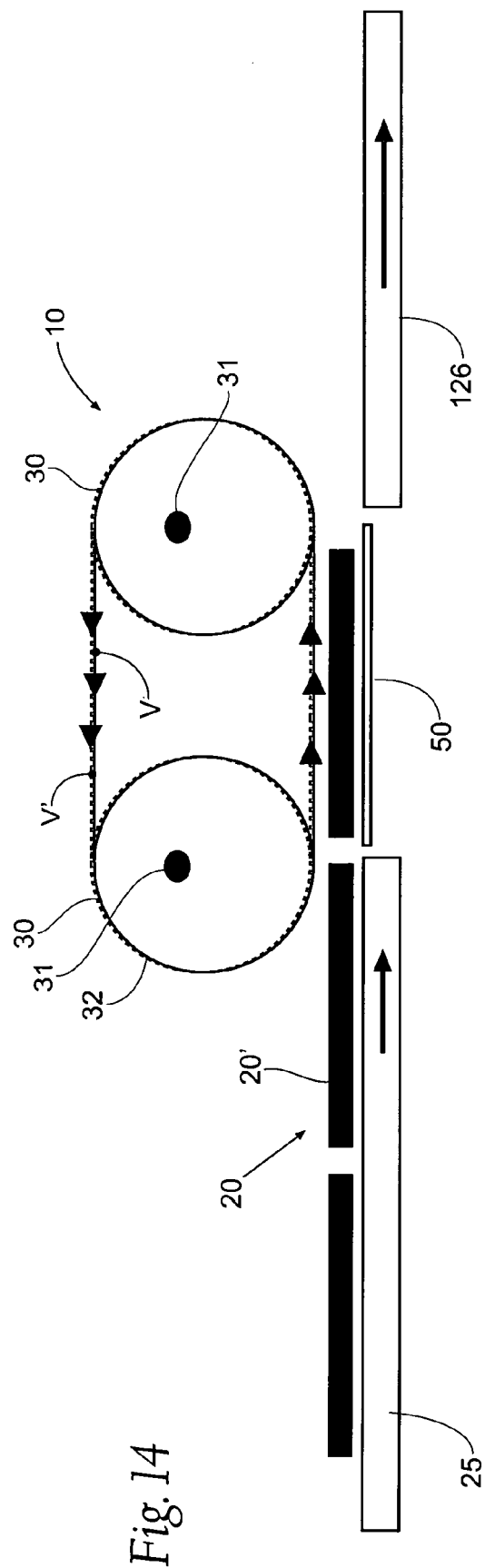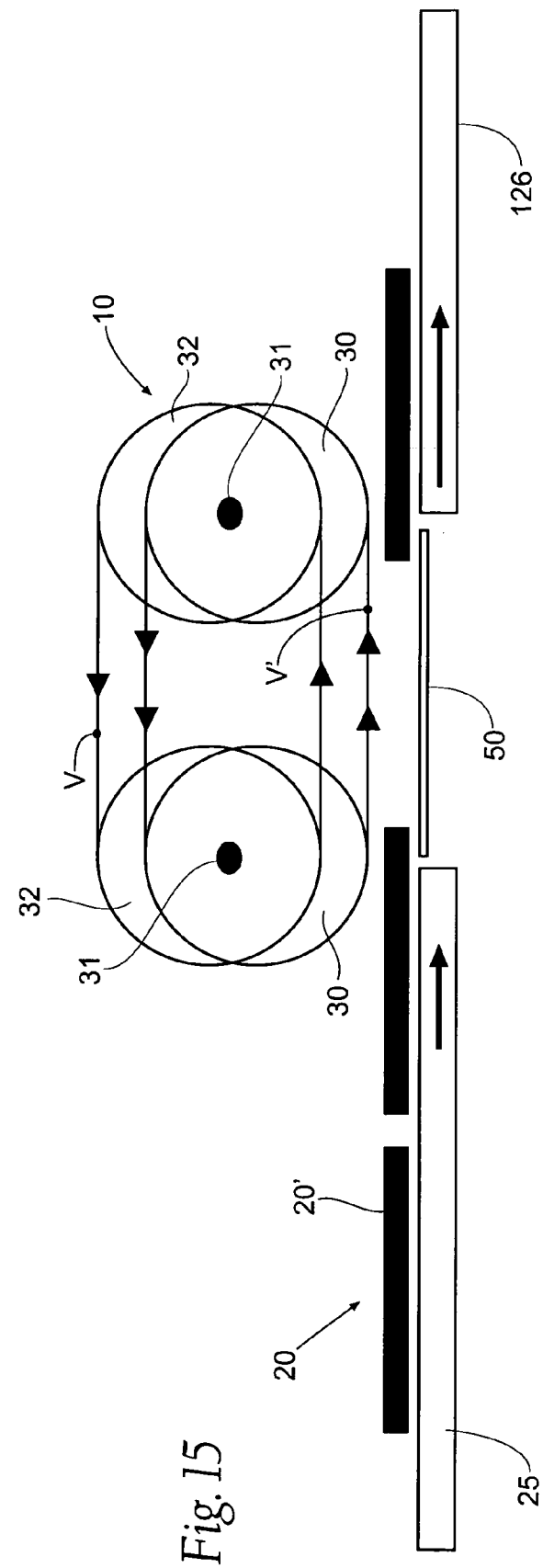
Fig. 14
Fig. 15

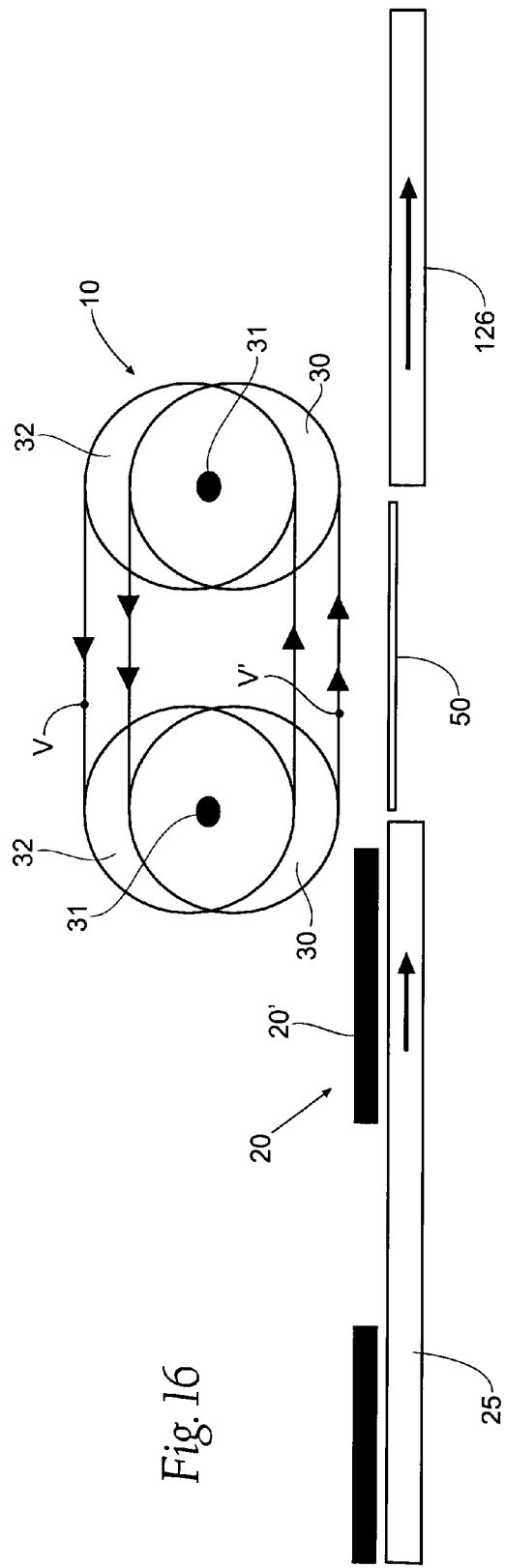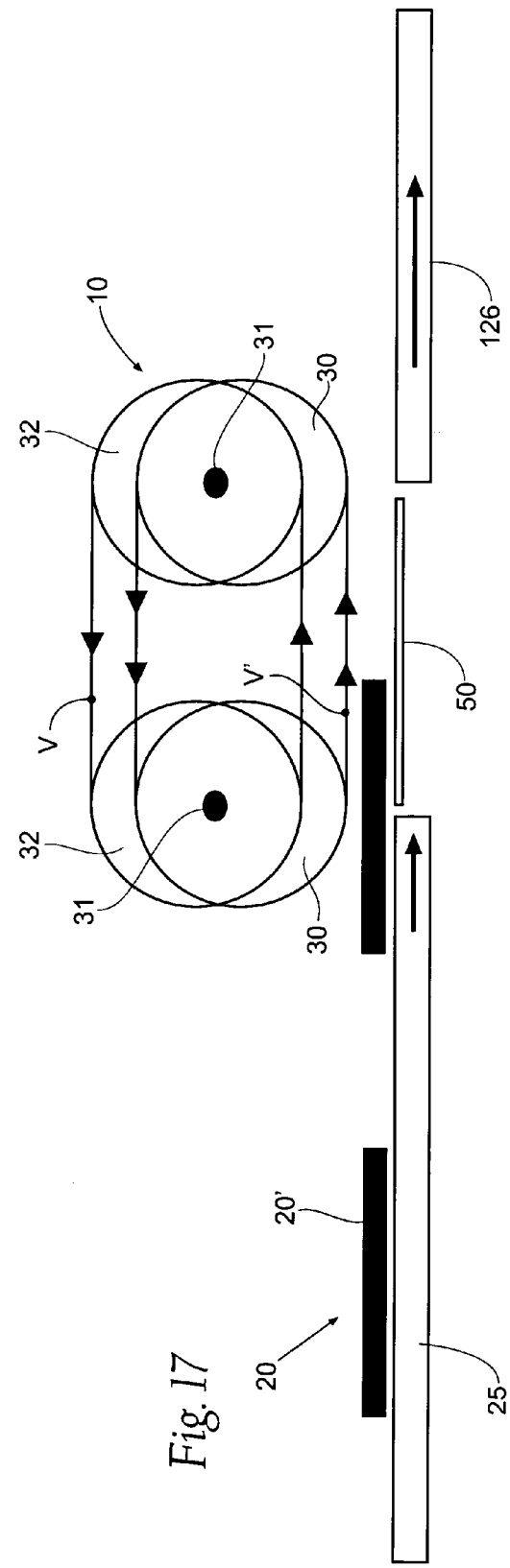
Fig. 16
Fig. 17

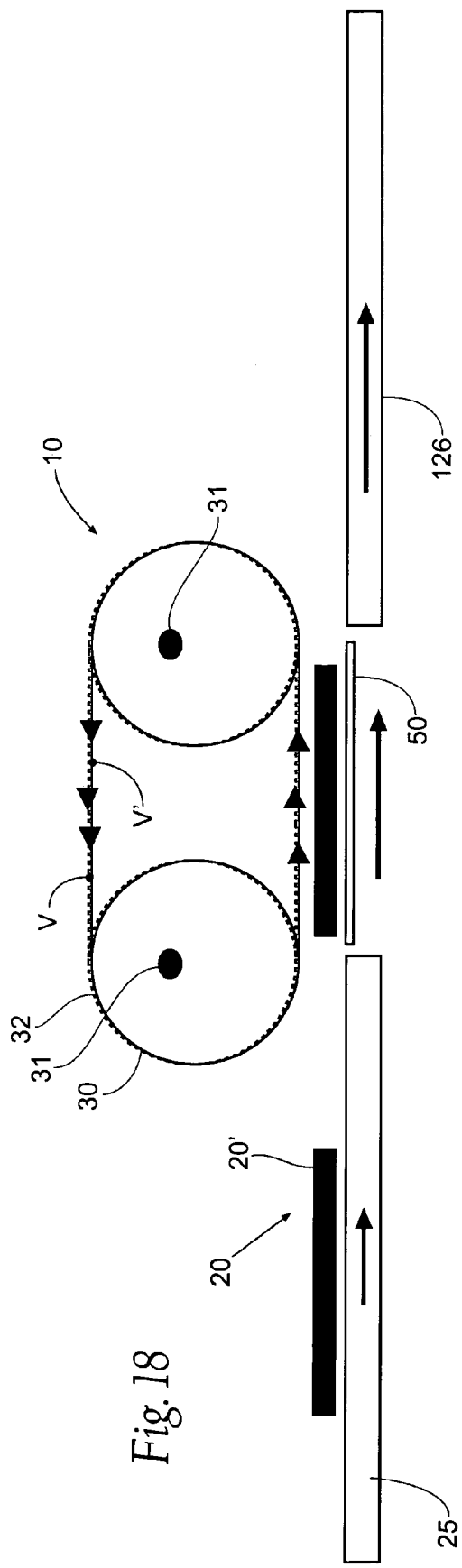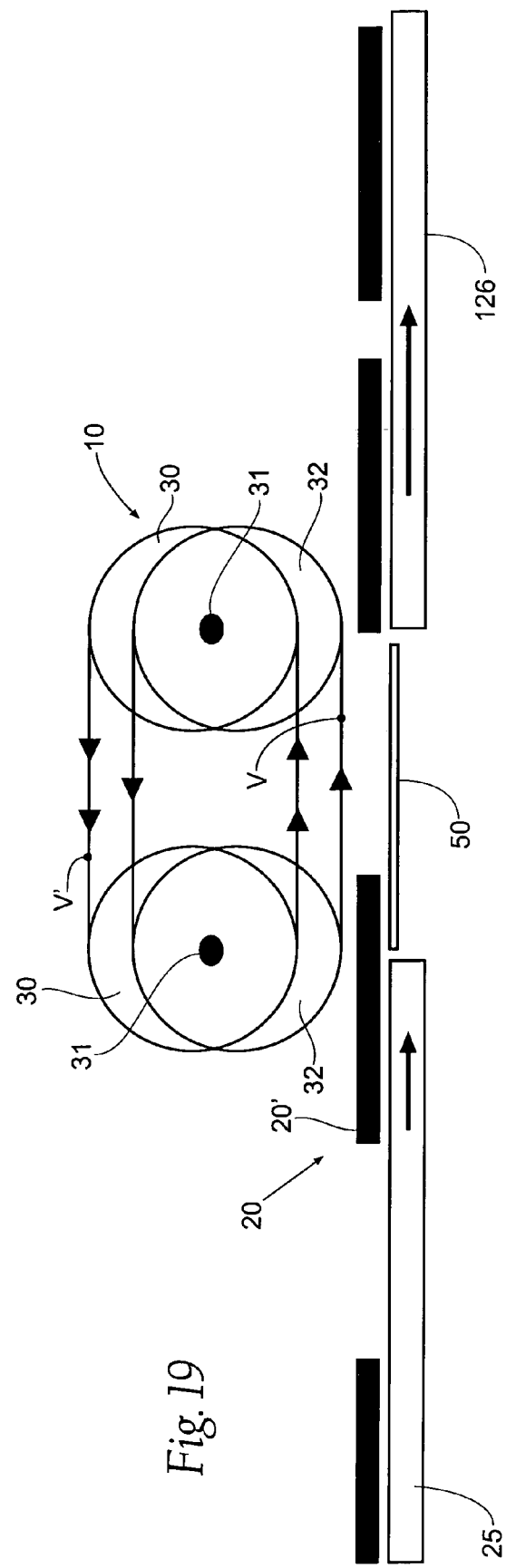

METHOD AND APPARATUS FOR CHANGING SPEED OR DIRECTION OF AN ARTICLE

RELATED APPLICATIONS

This application is a continuation-in-part of U.S. Ser. No. 11/104,316, filed 12 Apr. 2005, now U.S. Pat. No. 7,703,599 which claims the benefit of U.S. Provisional Ser. No. 60/563,511, filed 19 Apr. 2004, and entitled "Method and Apparatus for Reversing Direction of an Article".

BACKGROUND OF THE INVENTION

This invention relates to a method and apparatus for rapidly and accurately changing speed and/or reversing direction of a flat article. This invention is not limited to its preferred use, changing speed or reversing direction of a disposable diaper or sheet of paper; but instead the methods and apparatus' of the present invention may be used in wide ranging applications.

During manufacture of disposable diapers of the children's training pant type, or of the adult incontinence type, manufacturers typically process the diapers through a series of steps. For a variety of reasons, during the manufacturing process, it might be necessary to reverse direction of the article, from forward to reverse, or from forward to upside down to reverse, or from forward to downward etc.

It might also be necessary to speed up or slow down the speed of the article, or to change the spacing between a series of articles. By slowing incoming articles down, the spacing between two adjacent articles can be reduced. Similarly, by speeding up subsequent articles, spacing between two articles can be increased.

SUMMARY OF THE INVENTION

The present invention is used, for example, to controllably reverse the direction of the leading edge of a diaper panel as it is being cross folded. Typical cross folders used on high speed diaper lines may produce extremely high deceleration and reversal forces in the free tail end of the product being folded. One advantage provided by this invention is to reduce the acceleration forces felt by the product as it goes through the reversal process, by first carrying the article in a first direction by way of contact with the surface of a belt system which is moving in the first direction. At a point slightly before the expected reversal, the forward moving belt nip is opened and a reverse moving belt nip is engaged so that the product is stopped and then driven backwards by the second belt.

The present invention is particularly useful for products that may not be able to withstand high deceleration forces. For instance, a fluff filled adult diaper moving at a speed of more than 1000 feet per minute is stopped nearly instantly when it is cross folded. It has been calculated that the end of the product is subjected to accelerations as high as 65 Gs or 637 meters per second. The fluff contents of such a diaper could very well be destroyed by a "crack the whip" effect. The reversing conveyor of the present invention provides a controlled and driven reversal, wherein the product itself is not subjected to the same distribution of forces.

In one embodiment of the present invention, the positions of the conveyors or conveyor belts are swapped, reversed, or alternated using eccentric hubs on conveyor pulleys. Rotating the shaft that drive the eccentric hubs changes the effective centerline of these pulleys. In one embodiment, the eccentricity is such that rotating the shaft 180 degrees opens the outgoing belt nip and closes the ingoing belt nip. In another embodiment, the shafts are arranged so as to shift only one of the two belts, but each belt having its own dedicated shaft system. This would allow for the opening of one nip and the closing of the other nip to be adjustable relative to the other.

A method of reversing direction of an article is disclosed by engaging an article with a first belt to move the article in a first direction; disengaging the article from the first belt; and then engaging the article with a second belt to move the article in a second direction. An apparatus to reverse direction of an article is also disclosed by a first belt rotating in a first direction; a second belt rotating in a second direction; the first belt engaging an article at a first time while the second belt is disengaged with the article, the first belt disengaging the article at a second time, and the second belt engaging the article at a third time while the first belt is disengaged with the article.

In another embodiment, the present invention can be used to accelerate or decelerate articles, or to change the spacing between two adjacent articles. For instance, if two adjacent articles are provided closely together, the first article can be accelerated, and at a moment later, the second article can be accelerated. This lapse in time between acceleration of the first and second articles will cause the spacing between the two articles to increase.

Likewise, if two adjacent articles are provided further apart, the first article can be decelerated, and at a moment later, the second article can also be decelerated. This lapse in time between deceleration of the first and second articles will cause the spacing between the two articles to decrease.

These steps and advantages will be more evident with the following detailed description and drawings.

BRIEF DESCRIPTION OF THE DRAWINGS

FIGS. 1-11 show an apparatus for reversing direction of an article. FIG. 12—show an apparatus for changing the speed of an article and for changing the spacing between two adjacent articles.

FIG. 1 is a side view of an apparatus for reversing direction of an article, showing a first belt operating in a first direction, a second belt operating in a second direction, and an article whose direction is desired to be reversed;

FIG. 2 is a side view of the apparatus, with the article whose direction is desired to be reversed approaching the belts;

FIG. 3 is a side view of the apparatus, with the article whose direction is desired to be reversed being engaged by the first belt;

FIG. 4 is a side view of the apparatus, with the article whose direction is desired to be reversed being disengaged by the first belt and the second belt approaching the article for engagement;

FIG. 5 is a side view of the apparatus, with the article whose direction has been reversed by engagement with the second belt;

FIG. 6 is a side view of the apparatus, with the article whose direction has been reversed being disengaged by the second belt and discharged, and a second article approaching the apparatus for reversal;

FIG. 7 is a side view of an apparatus for reversing direction of an article, showing a first belt operating in a first direction, a second belt operating in a second direction, and an article whose direction is desired to be reversed.

FIG. 8 is a side view of one embodiment of a conveyor and conveyor pulleys, and an eccentric shaft.

FIG. 9 is a side view of an eccentric shaft coupled with four conveyors and conveyor pulleys.

FIG. 11 is a side view of another alternate embodiment showing a first belt operating in a first direction; a plate for engaging an article to discourage movement in a direction different than that encouraged by the belt.

FIGS. 12-21 show an apparatus for changing the speed of an article (either speeding up or slowing down) and for changing the spacing between two adjacent articles (either increasing the distance between two adjacent articles or decreasing the distance between two adjacent articles).

FIG. 12 is an apparatus for changing the speed and spacing of adjacent articles, showing a first belt operating in a first direction at a first speed, a second belt operating in the first direction at a second, faster speed, and an article whose speed is desired to be increased;

FIG. 13 is a side view of the apparatus for changing the speed and spacing of adjacent articles, with the articles whose speed and/or spacing between the following articles approaching the belts being engaged by the first belt;

FIG. 14 is a side view of the apparatus, with the first article whose speed and/or spacing between the following articles being disengaged by the first belt and the second belt approaching the article for engagement;

FIG. 15 is a side view of the apparatus for changing the speed and spacing of adjacent articles, with the article whose speed has been increased, and the spacing increased between it and the following article, by engagement with the second belt;

FIG. 16 is an apparatus for changing the speed and spacing of adjacent articles, showing a first belt operating in a first direction at a first speed, a second belt operating in the first direction at a second, slower speed, and an article whose speed is desired to be decreased approaching the belts;

FIG. 17 is a side view of the apparatus for changing the speed and spacing of adjacent articles, with the articles whose speed and/or spacing between the following articles approaching the belts being engaged by the first belt;

FIG. 18 is a side view of the apparatus, with the first article whose speed and/or spacing between the following articles being disengaged by the first belt and the second belt approaching the article for engagement;

FIG. 19 is a side view of the apparatus for changing the speed and spacing of adjacent articles, with the article whose speed has been decreased, and the spacing decreased between it and the following article, by engagement with the second belt;

FIG. 20 is an alternate embodiment of an apparatus for changing the speed and spacing of adjacent articles, this embodiment showing the articles being embraced by a top and a bottom set of belts.

FIG. 21 is a side view of one embodiment of a conveyor and conveyor pulleys, and an eccentric cam to open and close the relationship, or oscillating up and down to engage an article.

DESCRIPTION OF THE PREFERRED EMBODIMENT

Figure 3:
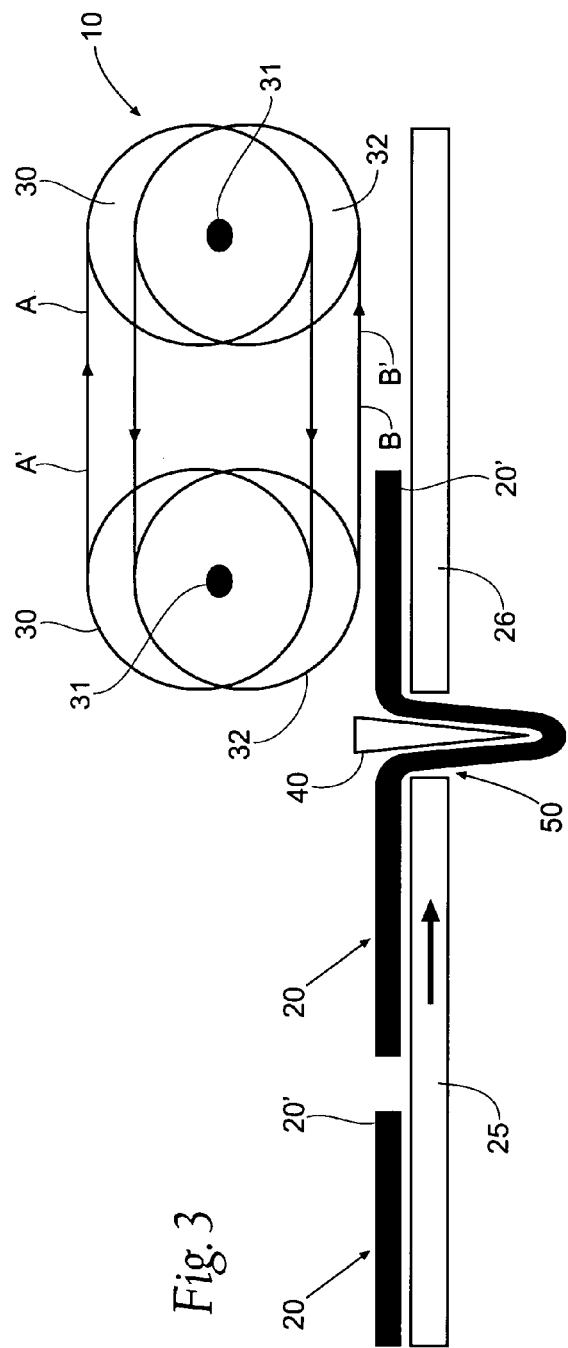

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention.

It is noted that the drawings, for clarity purposes so that the different elements can be seen, show the belts adjacent to but not contacting, the articles. This is merely for drawing clarity, it being understood that the belts move into contact with the articles when indicated by the text below, and out of contact with the articles when indicated by the text below.

Referring now FIG. 1, a side view is shown of an apparatus 10 for reversing direction of an article 20, showing a first belt B operating in a first direction B', a second belt A operating in a second direction A'. The article 20, which may be a diaper in a preferred use of one embodiment of the apparatus 10 and method of the present invention, approaches the apparatus 10 for instance by use of a conveyor 25, as depicted the article 20 moving to the right. As is common in the art, a cross folder 40, is used and will be described later to crimp the article 20 to encourage folding.

As will be discussed later, belt A may be carried by conveyor pulleys 30, belt B may be carried by conveyor pulleys 32. However, more or less conveyor pulleys may be utilized, or means other than belts A and B may be used to engage the article 20, such as nips, drums, or any other conveying means known in the art.

Referring now to FIG. 2, typical cross folders used on high speed diaper lines such as shown in FIG. 2 may produce extremely high deceleration and reversal forces in the free tail end 20' of the product being folded 20. To reduce the acceleration forces felt by the product 20 as it goes through the reversal process, depicted in the drawings as first forward to the right, reversing to second direction vertical downward, the article 20 is first carried the first direction (right as shown) by the conveyor 25, and then by engagement with contact with the surface of belt B moving in the first direction B'. (For clarity of illustration, the belts A and B are not shown directly engaged with the article 20, but instead showing slight separation that may or may not be present in physical embodiments of the present invention). Still referring to FIG. 2, the cross folder is shown approaching the article 20 to encourage folding of the article 20, the article 20 being supported by both conveyor 25 and stationary surface 26.

Referring now to FIG. 3, the cross folder 40 is shown impacting the article 20, both encouraging folding, and also sending a portion of the article downward through void 50 down its later expected path. At this point, the article 20 is still moving to the right as shown, both by conveyor 25 and by belt B moving in direction B'.

Figure 4:
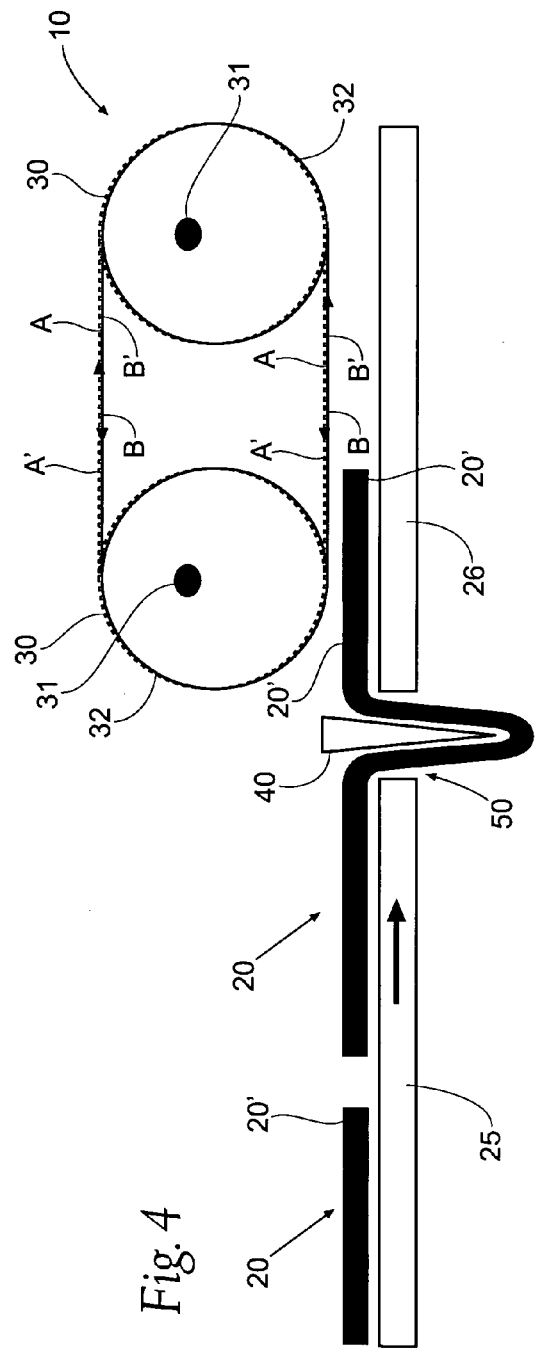

Referring now to FIG. 4, at a point slightly before the expected reversal of the tail end 20' of the article 20, the belt B has disengaged with the article 20 and belt A moving in direction A' (reverse direction of B') is approaching the article 20. At this point, cross folder 40 remains positioned as earlier in relation to the article 20.

Without the present invention, products that may not be able to withstand high deceleration forces would be exposed to very high deceleration at this point of reversal. For instance, a fluff filled adult diaper moving at a speed of more than 1000 feet per minute is stopped nearly instantly when it is cross folded. It has been calculated that the free end 20' of the product 20 would have been subjected to accelerations as high as 65 Gs or 637 meters per second. The fluff contents of such a diaper could very well be destroyed by a "crack the whip" effect. The reversing conveyor of the apparatus 10 provides a controlled and driven reversal, wherein the article 20 is not subjected to the same distribution of forces.

Figure 5:
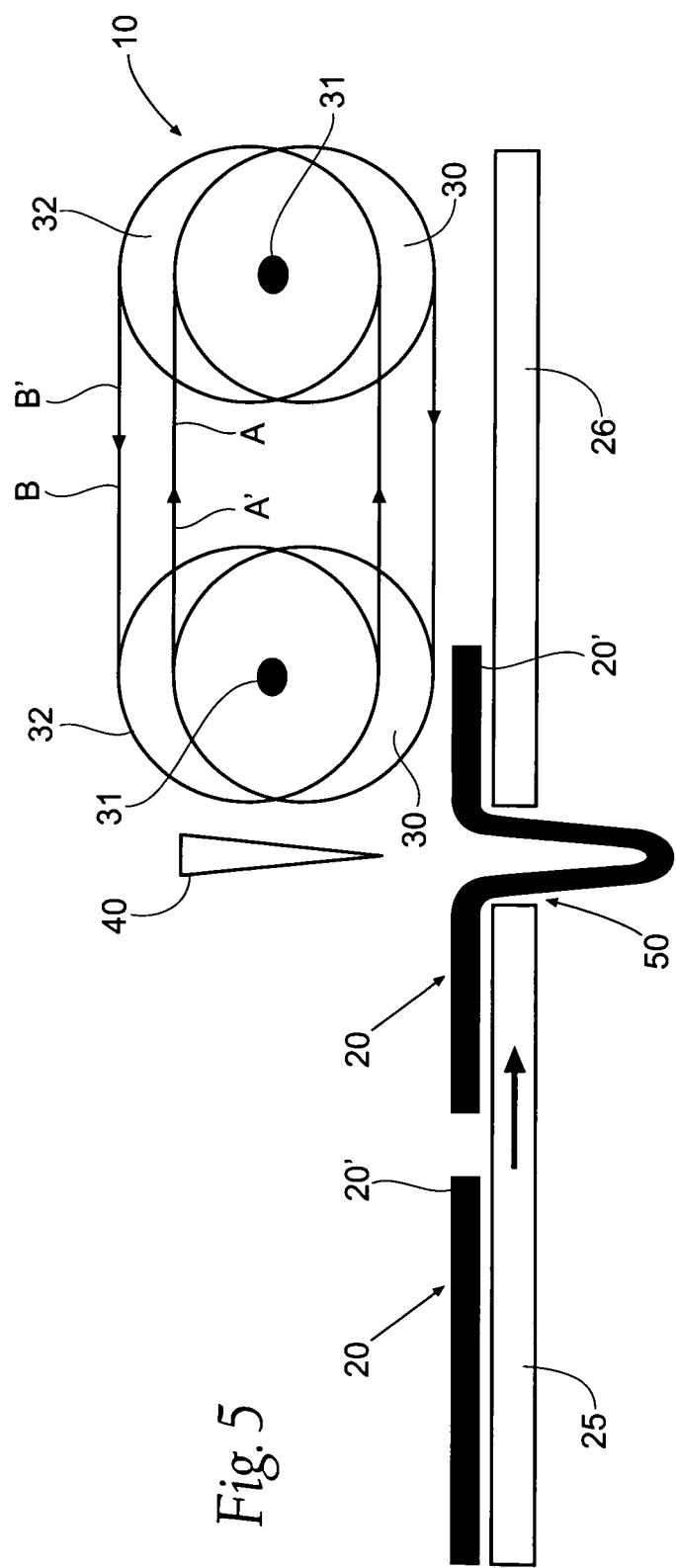

Referring now to FIG. 5, belt A has engaged the free end 20' of the article 20, and the free end 20' of the article 20 is stopped and then driven backwards by the second belt A moving in direction A'. At this point, the two ends of the article 20 are moving toward each other, and the direction of the free end 20' of the article 20 has been successfully reversed. At this point, cross folder 40 is being withdrawn from the article 20.

Figure 6:
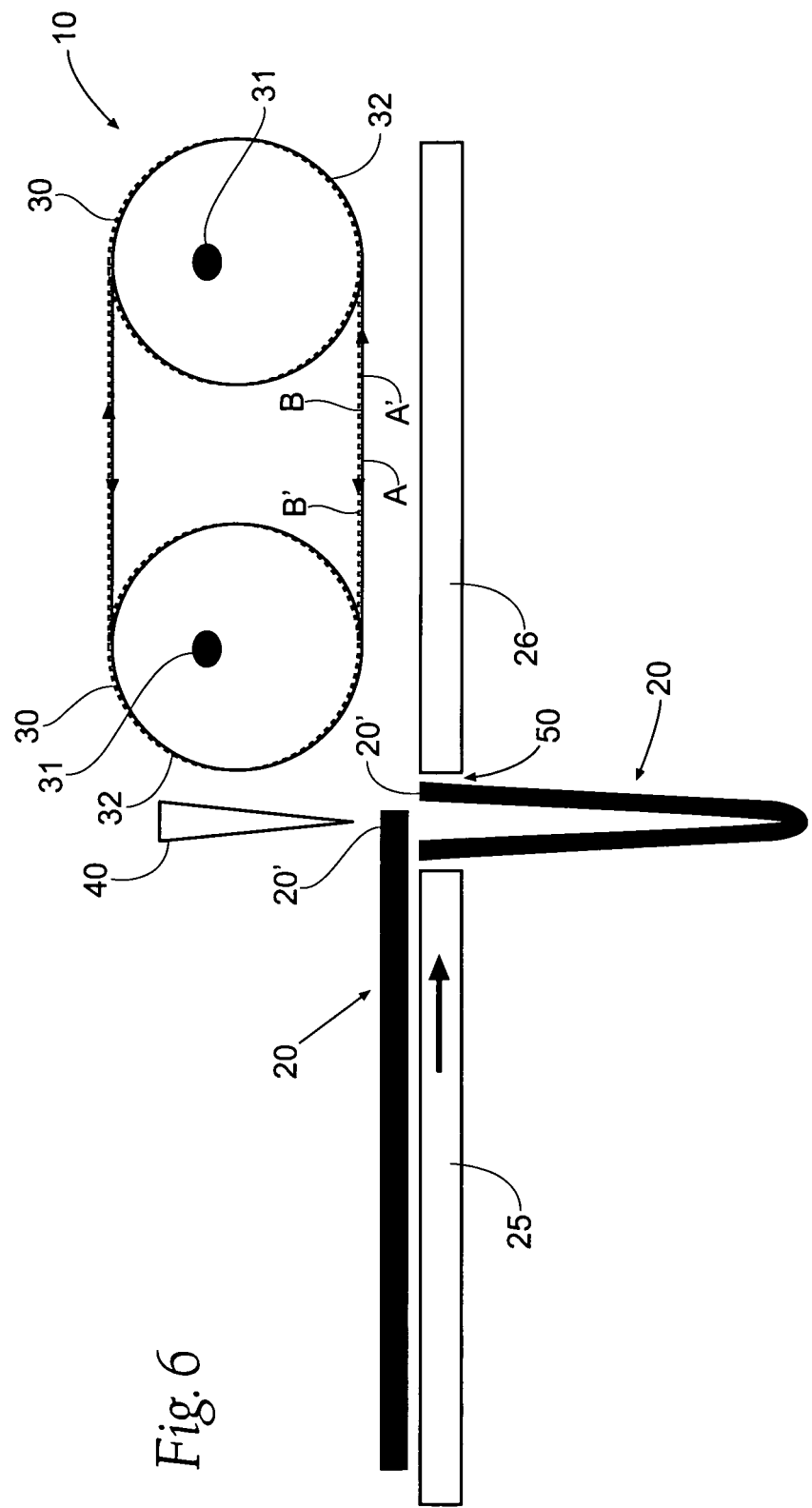

Referring now to FIG. 6, a side view of the apparatus 10 is shown, with the article 20 whose direction has been reversed being disengaged by the second belt A and discharged through the void 50. At this point, a second article 20 is approaching the apparatus 10 for its eventual reversal as described above.

Figure 7:
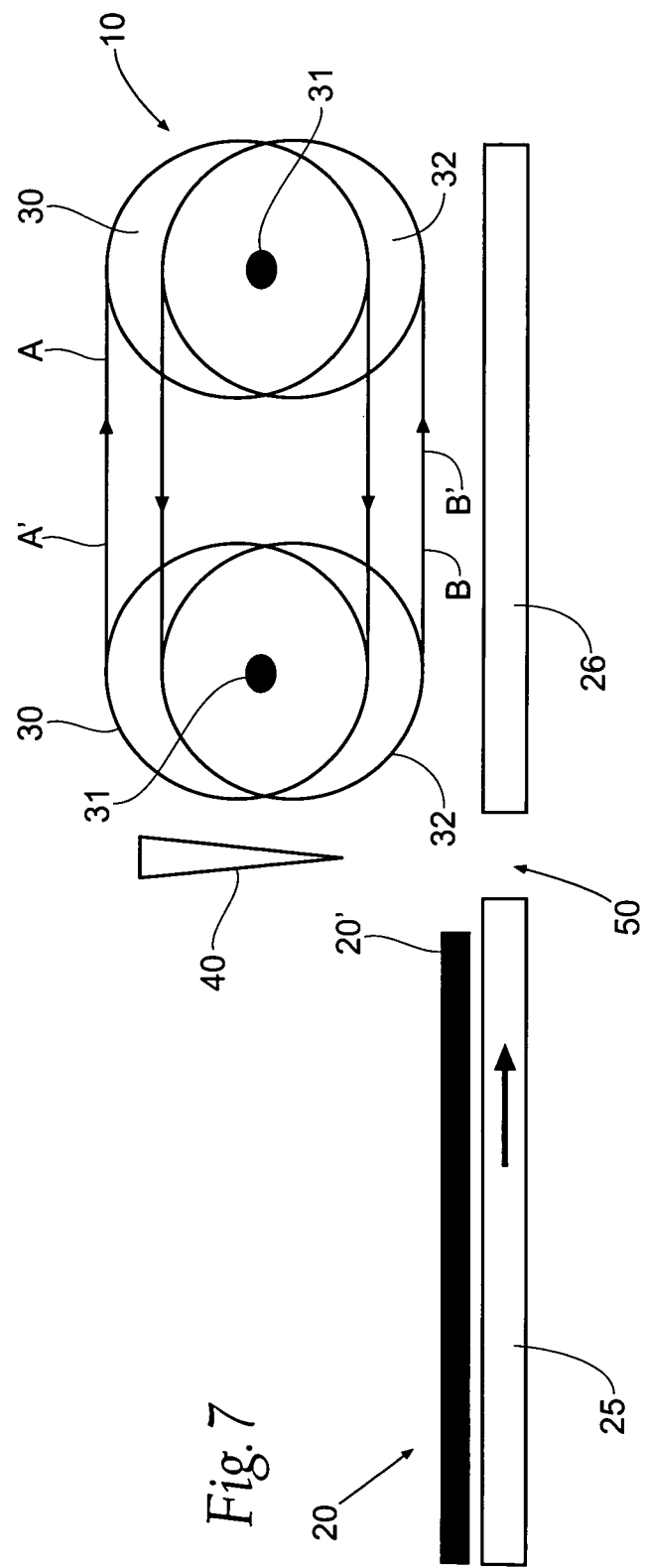

Referring now to FIG. 7, a side view of the apparatus 10 is shown, and the apparatus has returned to the same condition depicted in FIG. 1, prepared to reverse the direction of the second article 20, the direction of first article 20 already being changed, first article 20 continuing down its intended path for further processing.

There are several timing and synchronization considerations to consider in the operation of the apparatus 10. First, the timing of the cross folder 40 is preferably such that the cross folder cycles once for each article 20 passed through the apparatus 10. It may be preferable to time the cross folder 40 to impact the article 20 in the middle of the article 20, but this may be varied in accordance with user preference.

Another timing consideration is that it is preferred that each belt A and B operate in a speed equal to the conveyor 25. This is preferred because the free end 20' will be traveling the same speed in the same direction B' as its opposing end while engaged by belt B. This is also preferred so that both ends, free end 20' and its opposing end are traveling toward void 50 in opposite directions while free end 20' is being engaged by belt A. Therefore belt A and conveyor 25 should be traveling the same speed in the same direction, while belt B and conveyor 25 should be traveling the same speed in opposite directions.

Another timing consideration is that folded reversed articles 20 should be withdrawn from the apparatus 10 at the same rate as unfolded articles 20 enter the apparatus 10.

As a last timing consideration, each cycle of the present methodology comprises one article 20 being fed into the apparatus 10, engaging the article 20 with belt B, disengaging belt B while engaging the article with belt A, then discharging article 20. Therefore, for each cycle, belts A and B, and cross folder 40 act in synchronization of one engagement per cycle. The operation and implementation of these synchronization considerations is well known in the art and will not be described herein.

In one embodiment of the present invention, conveyors or conveyor belts A and B are reversed using eccentric hubs 30 and 32. Rotating the shaft 31 that drive the eccentric hubs 30 and 32 changes the effective centerline of these pulleys. In one embodiment, the eccentricity is such that rotating the shaft 31 180 degrees engages belt A disengages belt B. In another embodiment (not shown), shafts are arranged so as to shift only one of the two belts A or B, but each belt A and B having its own dedicated shaft system. This would allow for the opening of one nip and the closing of the other nip to be adjustable relative to the other.

Figure 8:
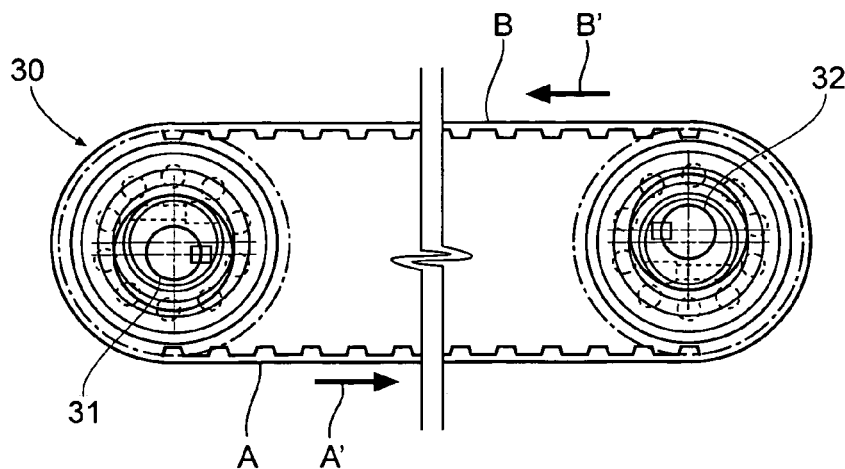

Referring now to FIG. 8, conveyor belts A and B are shown driven by hubs 30 and 32.

Figure 9:
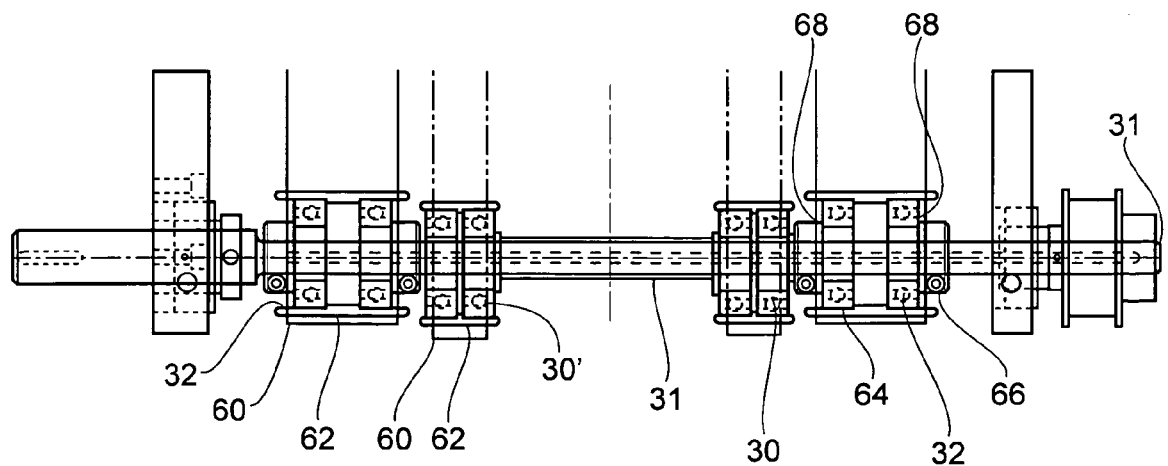

Referring now to FIG. 9, another side view is shown of the shaft 31 carrying hubs 30 and 32 (4 shown). Also shown are timing belts 60, rollers 62, ball bearings 64, collars clamps 66, and cams 68 it being understood that each hub 30 and 32 may be similarly equipped. In the view shown, it can be seen that hubs 30, situated between hubs 32, are in the lower position. Rotating shaft 31, would cause hubs 30 to raise, while also causing hubs 32 to lower. In this sense, the shaft 31 rotatably causes the first hub 30 and said second hub 30 and 32 to alternately raise and lower.

Figure 10A:
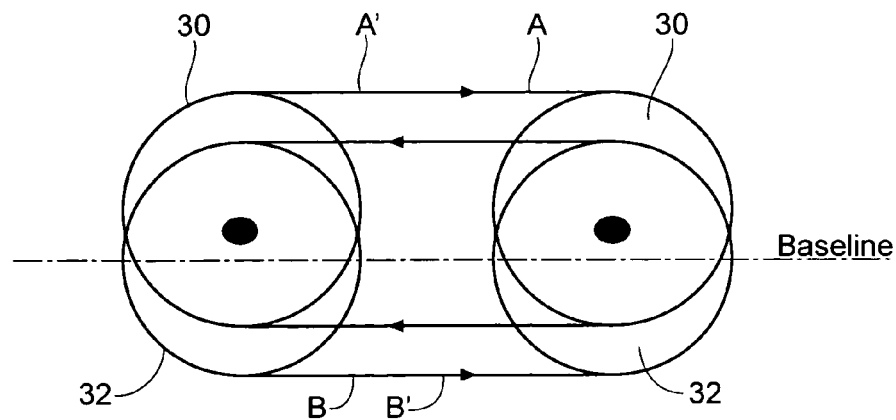
FIGS. 10a and 10b are side views of an alternate embodiment of an apparatus for reversing direction of an article, showing a first belt operating in a first direction, a second belt operating in a second direction, the first belt stationary and the second belt oscillating up and down to engage an article.
Figure 10B:
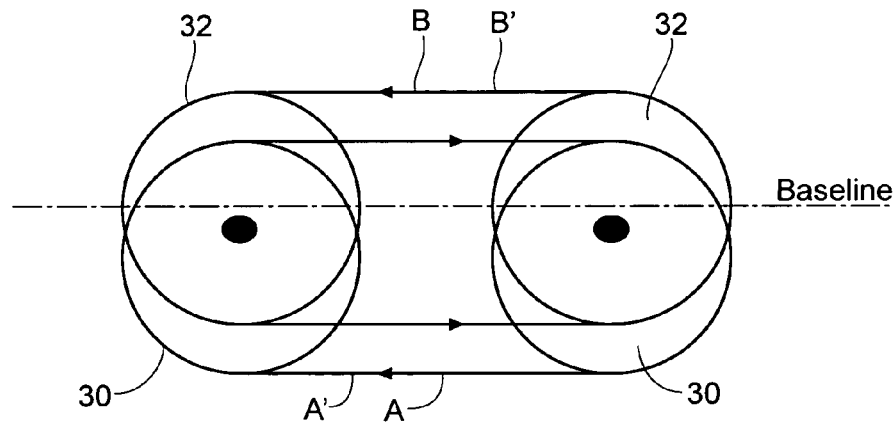

Referring now to FIGS. 10a and 10b side views of an alternate embodiment of an apparatus for reversing direction of an article are shown. In this embodiment, a first belt A operates in a first direction A' as previously described, and a second belt B operating in a second direction B' as previously described. In this embodiment however, the hubs 32 remain stationary vertically relative to the baseline pictured, and the hubs 30 move up and down vertically relative to the baseline to engage an article (not shown). In this manner, the belts A and B still alternately engage the article and the engagement, including the maneuvering of the cross folder 40, the belt 25 and other timing aspects remain the same as in the maneuvering of the hubs 30 and 32 synchronously as described above.

Figure 11:
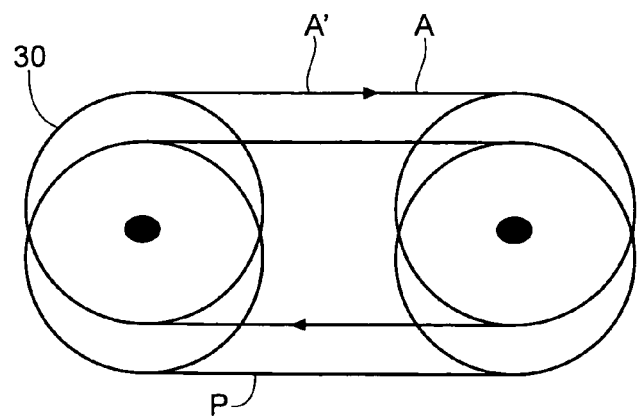

Referring now to FIG. 11, an alternate embodiment of an apparatus for reversing direction of an article is shown, showing a first belt A operating in a first direction A', and a plate P that is not required to rotate with reference to previously described belts. In this embodiment, there is only directional assistance applied to the article 20 in one direction (A'), and the belt A is drawn into contact 20 with product (not shown) when directional reversal is required.

FIGS. 12-21 show an apparatus for changing the speed of an article 20 (either speeding up or slowing down) and for changing the spacing between two adjacent articles (either increasing the distance between two adjacent articles or decreasing the distance between two adjacent articles).

In this embodiment, the present invention can be used to accelerate or decelerate articles 20, or to change the spacing between two adjacent articles 20. For instance, if two adjacent articles 20 are provided closely together (e.g., FIG. 12), the first article can be accelerated (e.g., FIG. 14), and at a moment later, the second article can be accelerated (e.g., FIG. 15). This lapse in time between acceleration of the first and second articles will cause the spacing between the two articles to increase.

Likewise, if two adjacent articles are provided further apart, the first article can be decelerated, and at a moment later, the second article can also be decelerated. This lapse in time between deceleration of the first and second articles will cause the spacing between the two articles to decrease.

Referring now to FIG. 12, an apparatus for changing the speed and spacing of adjacent articles, showing a first belt operating in a first direction at a first speed, a second belt operating in the first direction at a second, faster speed, and an article whose speed is desired to be increased is shown.

Similar to the operation of the reversing direction embodiment of FIGS. 1-11, the shaft 31 that drives the eccentric hubs 30 and 32 changes the effective centerline of these pulleys. In one embodiment, the eccentricity is such that rotating the shaft 31 180 degrees engages belt A disengages belt B. In another embodiment (not shown), shafts are arranged so as to shift only one of the two belts A or B, but each belt A and B having its own dedicated shaft system. This would allow for the opening of one nip and the closing of the other nip to be adjustable relative to the other.

In this embodiment, the belt V driven by hub 32 travels at a first speed V, and the belt V' driven by hub 30 travels at a second, faster speed V'.

Referring now to FIG. 13, a side view of the apparatus for changing the speed and spacing of adjacent articles 20, with the articles 20 whose speed and/or spacing between the following articles approaching the belts V and V' being engaged by the first belt V is shown. This belt V is preferably traveling substantially the same speed as conveyor 25 to ensure a smooth, relatively shear free transition off of the conveyor 25 onto dead plate or guiding structure 50.

Referring now to FIG. 14, a side view of the apparatus, with the first article 20 whose speed and/or spacing between the following articles being disengaged by the first belt V and the second belt V' approaching the article for engagement is shown. The second belt V' then engages the article 20 and speeds it to the faster V' speed, preferably traveling substantially the same speed as conveyor 126 to ensure a smooth, relatively shear free transition off of the dead plate or guiding structure 50 onto conveyor 126.

Referring now to FIG. 15, a side view of the apparatus for changing the speed and spacing of adjacent articles 20, with the article 20 whose speed has been increased shown deposited onto conveyor 126, and the spacing increased between it and the following article 20, by engagement with the second belt V' is shown. The belts V and V' then cycle back to the position shown in FIG. 12, prepared for another incoming article 20 to be sped up and placed on conveyor 126.

Referring now to FIG. 16, an apparatus for changing the speed and spacing of adjacent articles 20 is shown. In this embodiment, the articles are traveling at an initially faster speed V' and at a greater spacing than the articles of the embodiment shown in FIGS. 12-15. If it is desired to slow the articles and/or reduce their spacing between subsequent articles, this embodiment can be employed.

Referring to FIG. 17, the article 20 approaches the belt V' traveling substantially the same speed as conveyor 25, which is faster than conveyor 126 upon which the article 20 will exit. As shown in FIG. 18, the article is first engaged by belt V' at the faster speed and onto the dead plate 50, where belt V' disengages the article 20. Next, as shown in FIG. 19 the article 20 is engaged by the slower belt V and the article is then transferred onto the conveyor 126 at substantially the same speed as both belt V and conveyor 126. As is evident from FIG. 19, the articles 20 will then be spaced more closely together than they were upon entering the system, and also traveling slower, at the rate of conveyor 126, which in this embodiment is slower than the conveyor 25.

Figure 20:
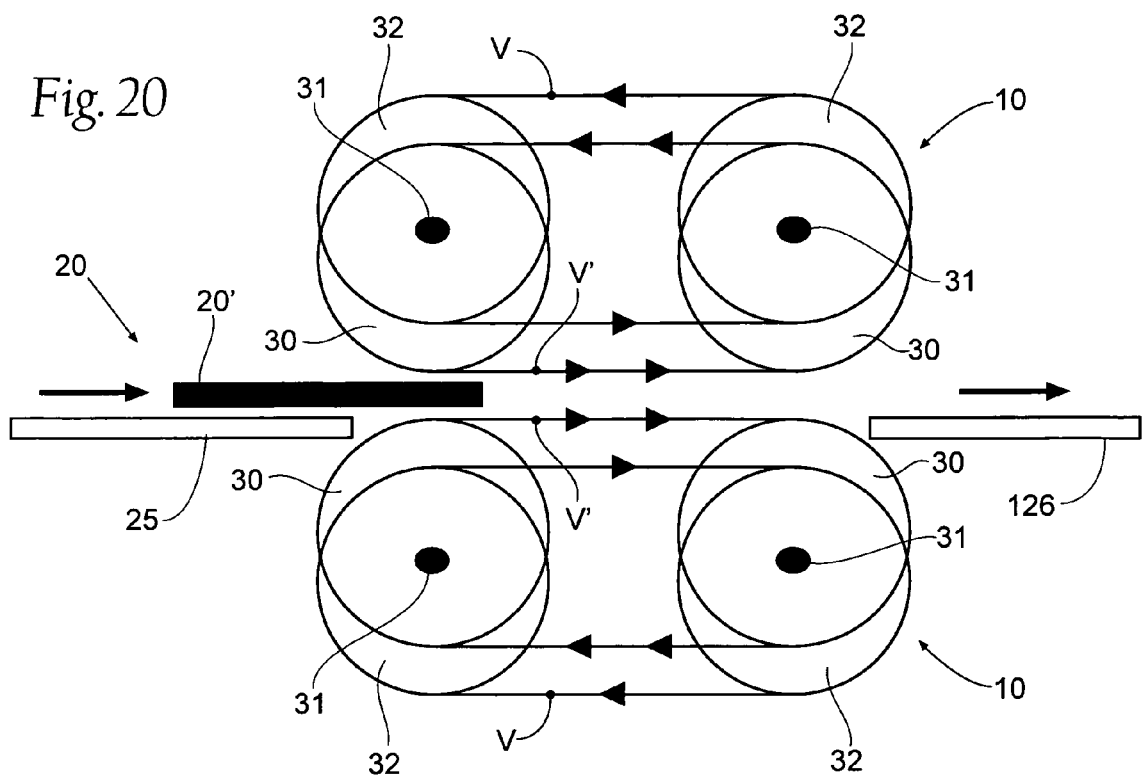

Referring now to FIG. 20, an embodiment of an apparatus for changing the speed and spacing of adjacent articles is shown. In this embodiment, the articles can be operated upon without the assistance of the dead plate 50, and instead the articles can be sandwiched between two belts operating at the same speed.

Figure 21:
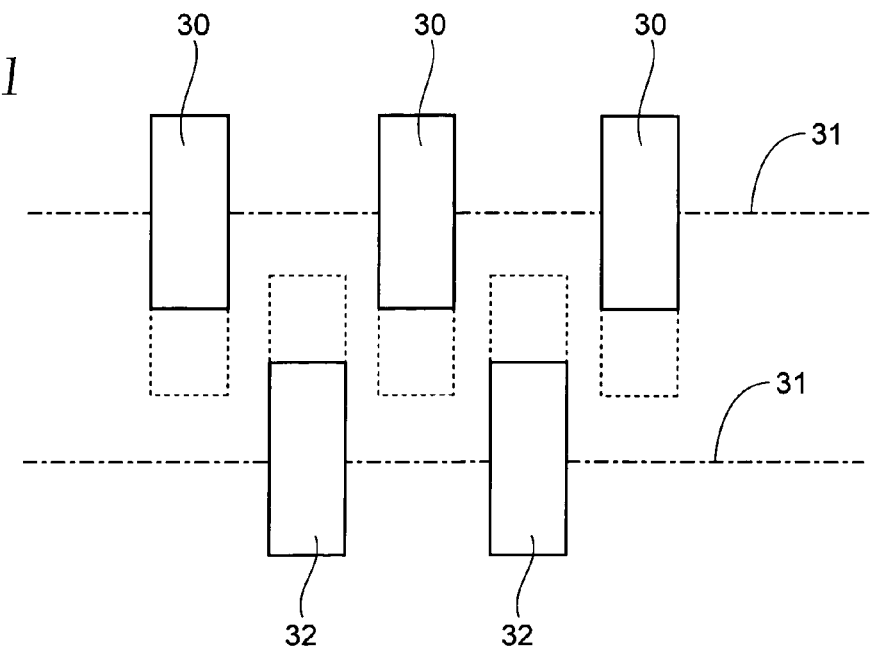

Referring now to FIG. 21, a side view of one embodiment of a conveyor and conveyor pulleys, and an eccentric cam to open and close the relationship, or oscillating up and down to engage an article is shown. Similar to FIG. 9, two rotating shafts 31 are provided, and each can be rotating in eccentric fashion to raise and lower hubs 30 and 32, in order to introduce the belts carried thereby (not shown) in the desire fashion, depending on the speeding or slowing, or reversing operations described above.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:

1. An apparatus for changing speed of a series of articles comprising:
   a means for carrying a bottom side of a series of articles to a speed change device at a first speed, said articles each separated by a first spacing,
   a means for carrying said bottom side of series of articles from said speed change device at a second speed, said articles separated by a second spacing,
   said speed change device comprising:
   a first belt rotating in a first direction at approximately said first speed;
   said first belt engaging a top side of a first article during a first time period of contact to urge said first article in a forward direction at approximately said first speed;
   said first belt operating between said means for carrying a bottom side of a series of articles to a speed change device at a first speed and said means for carrying said bottom side of series of articles from said speed change device at a second speed,
   a second belt rotating in said first direction at substantially said second speed, said second speed different than said first speed;
   said second belt engaging said top side of said first article during a second time period of contact, said second time period of contact after said first period of contact, to urge said first article in said first direction at substantially said second speed;
   said article being acted upon by only one of said belts during said first time period and said second time period;
   said second belt discharging said series of articles to said means for receiving said series of articles.

2. An apparatus according to claim 1, wherein said first speed is slower than said second speed.

3. An apparatus according to claim 1, wherein said second speed is slower than said first speed.

\* \* \* \* \*